(12) United States Patent
Goldstein

(10) Patent No.: US 7,326,220 B1
(45) Date of Patent: Feb. 5, 2008

(54) TOOL FOR REMOVING INTRAOCULAR FOREIGN BODIES

(75) Inventor: Burton G Goldstein, Tampa, FL (US)

(73) Assignee: University of South Florida, Tampa, FL (US)

( * ) Notice: Subject to any disclaimer, the term of this patent is extended or adjusted under 35 U.S.C. 154(b) by 369 days.

(21) Appl. No.: 10/711,226

(22) Filed: Sep. 2, 2004

Related U.S. Application Data

(60) Provisional application No. 60/481,322, filed on Sep. 2, 2003.

(51) Int. Cl.
*A61B 17/22* (2006.01)
*A61B 17/24* (2006.01)
*A61B 17/26* (2006.01)
*A61F 9/00* (2006.01)
*A61M 29/00* (2006.01)

(52) U.S. Cl. ............... 606/113; 606/107; 606/159; 606/114; 606/200; 606/127

(58) Field of Classification Search ............... 623/6.12; 606/107, 113, 114, 200, 127, 159
See application file for complete search history.

(56) References Cited

U.S. PATENT DOCUMENTS

| 5,891,153 | A | * | 4/1999 | Peterson | ............... 606/107 |
| 6,652,537 | B2 | * | 11/2003 | Mercereau et al. | ......... 606/127 |
| 2003/0135221 | A1 | * | 7/2003 | Sabet | ............... 606/107 |

* cited by examiner

*Primary Examiner*—Loan H. Thanh
*Assistant Examiner*—Amy T. Lang
(74) *Attorney, Agent, or Firm*—Ronald E. Smith; Smith & Hopen P.A.

(57) ABSTRACT

A surgical tool captures and removes very large intraocular foreign bodies from the eye. An elongate bore is formed in an elongate base that is held in the palm of a hand. A user retracts a foreign body capturing device including a handle, rim, and net into the elongate bore by sliding a thumb-engagable control member in a first direction. The device is extended by sliding the control member in a second direction opposite to the first. The rim is formed of a material having memory so that it expands into an elliptical shape when extended from the elongate bore. The net depends from the rim and is used to capture intraocular foreign bodies. Gradual curves at the trailing end of the rim facilitate its re-entry into the elongate bore when a foreign body is captured in the net. The incision in the eye is small.

5 Claims, 3 Drawing Sheets

TOOL FOR REMOVING INTRAOCULAR FOREIGN BODIES

CROSS-REFERENCE TO RELATED APPLICATION

This application claims priority from U.S. provisional application Ser. No. 60/481,322, entitled: "Intraocular Foreign Body Basket, filed Sep. 2, 2003.

BACKGROUND OF THE INVENTION

1. Field of the Invention

This invention relates, generally, to surgical tools. More particularly, it relates to a surgical tool used by retina specialists for extracting intraocular foreign bodies.

2. Description of the Prior Art

Surgical tools for removing intraocular bodies are in common use. If the intraocular body is small to medium in size, its removal is not particularly problematic because the known tools are effective and generally safe to use. However, the removal of large or very large intraocular bodies is more problematic because the tools for removing the small to medium sized intraocular bodies have little or no utility in removing large or very large bodies.

The tools for removing large to very large intraocular bodies are quite large and a large incision is required to accommodate such tools. Large incisions are undesirable so there is a need for a tool that removes very large intraocular bodies but which does not require the making of a large incision in the eye.

However, in view of the prior art considered as a whole at the time the present invention was made, it was not obvious to those of ordinary skill in the medical arts how the needed surgical tool could be provided.

SUMMARY OF INVENTION

The long-standing but heretofore unfulfilled need for a surgical tool that removes very large intraocular foreign bodies is now met by a new, useful, and non-obvious invention. The novel surgical tool for capturing and removing intraocular foreign bodies includes an elongate base. An elongate bore is formed in the elongate base and has a leading end in open communication with a leading end of the elongate base. A foreign body capturing means is slideably received within the elongate bore and includes an elongate handle, a rim, and a net. A control member is connected to the foreign body capturing means for controlling its instantaneous position. The foreign body capturing means has a fully retracted position where it is substantially received within the elongate bore, a fully extended position where it is fully extended from the elongate bore, and an infinite number of functional positions of adjustment, therebetween.

An elongate slot is formed in the elongate base in parallel relation to the elongate bore. The elongate slot has a length substantially equal to a length of the elongate bore. The control member is slideably mounted to a top wall of the elongate base and has a fully retracted position, a fully extended position, and an infinite number of functional positions of adjustment therebetween. A rigid rod interconnects the control member and the handle of the foreign body capturing means. The fully retracted position of the control member corresponds to the fully retracted position of the foreign body capturing means and the fully extended position of the control member corresponds to the fully extended position of the foreign body capturing means.

The elongate slot has a width less than a width of the elongate bore. A truncate slot is formed in a bottom wall of the elongate base in parallel relation to the elongate bore and has a length less than the length of the elongate bore. The truncate slot has a leading end in open communication with the leading end of the elongate base. The net has an upper end mounted about a perimeter of the rim and has a main body, integral with its upper end, that depends from the upper end when the foreign body capturing means is in the fully retracted position, the fully extended position, and the infinite number of functional positions of adjustment therebetween.

The handle is bifurcated at a leading end thereof to form a pair of branches including a first branch having a first arcuate curve formed therein and a second branch having a first arcuate curve formed therein. The first branch first arcuate curve and the second branch first arcuate curve diverge from one another in a common plane when in repose. The first branch further has a second arcuate curve formed therein and the second branch further has a second arcuate curve formed therein. The respective second arcuate curves of the first and second branches converge toward one another when in repose so that the first and second branches cooperate to form the rim of the foreign body capturing means. The rim has a substantially linear configuration when fully received within elongate bore and has an elliptical configuration when fully extended from the elongate bore. The first arcuate curve of the first branch and the first arcuate curve of the second branch cooperate with one another to facilitate entry of the rim into the elongate bore when the foreign body capturing means is moved from its fully extended configuration to its fully retracted configuration.

The rim is preferably formed of a metallic or polymeric material having flexibility, resilience, and memory. The net is preferably formed of a fabric mesh.

The invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which.

DETAILED DESCRIPTION OF THE PREFERRED EMBODIMENT

Figure 1:
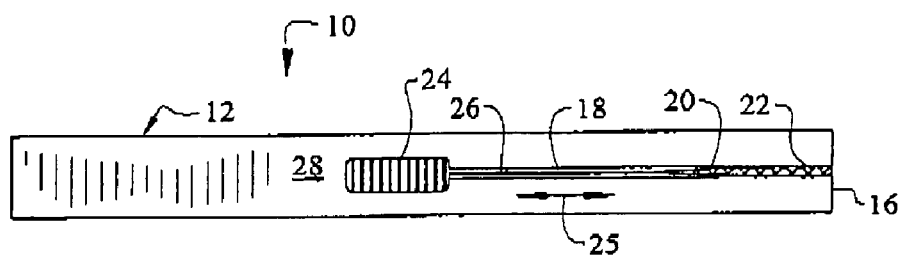
FIG. 1 is a top plan view of an illustrative embodiment of the invention in its fully retracted configuration.
Figure 2:
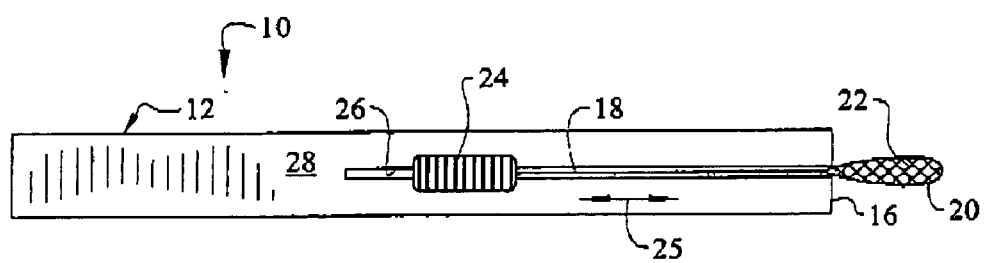
FIG. 2 is a top plan view of the illustrative embodiment in its partially extended configuration.
Figure 3:
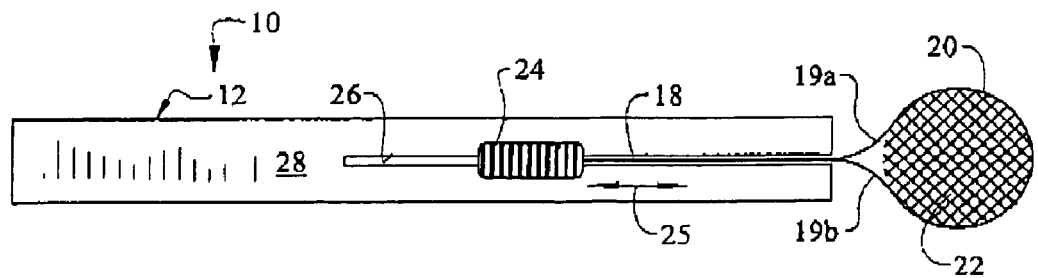
FIG. 3 is a top plan view of the illustrative embodiment in its fully extended configuration.

Referring now to FIGS. 1-3, it will there be seen that an illustrative embodiment of the invention is denoted as a whole by the reference numeral 10.

Surgical tool 10 includes an elongate base 12 that is sized for comfortable holding in a human hand.

Elongate bore 14 (FIG. 6) is formed in base 12, preferably coincident with the longitudinal axis of symmetry of base 12 but such positioning is not critical. Bore 14 is a blind bore, extending to about mid-length of base 12 and having a leading end in open communication with the leading end of tool 10 as denoted by the reference numeral 16.

Two (2) components of a foreign body capturing means are fully received within elongate bore 14 when tool 10 is in its fully retracted configuration as depicted in FIG. 1, and a third component of said foreign body capturing means is partially received therewithin. The two components fully received within said bore are a linear-in-configuration handle 18 and a rim 20. The third component is a net or basket 22 having an upper edge that is mounted about the periphery of rim 20.

Handle 18 is preferably formed of a rigid metallic material although it may also be formed of plastic or any other material. Rim 20 is preferably formed of a flexible and resilient polymeric material having memory. Net or basket 22 preferably has a mesh construction such as a fabric mesh.

Rim 20 is formed integrally with handle 18 at the leading end of said handle. When fully retracted within elongate bore 14, rim 20 is constrained to have a substantially linear configuration like that of handle 18. Thus, it is said to have a narrow profile. However, when partially extended from elongate bore 18, as depicted in FIG. 2, rim 20 begins to open under its inherent bias into a substantially circular or elliptical shape. When fully extended as depicted in FIG. 3, rim 20 has a fully open, substantially circular or elliptical shape. Significantly, rim 20 passes through a small incision made in the eye while still in its narrow profile configuration and does not fully open until it has passed through the incision.

Figure 4:
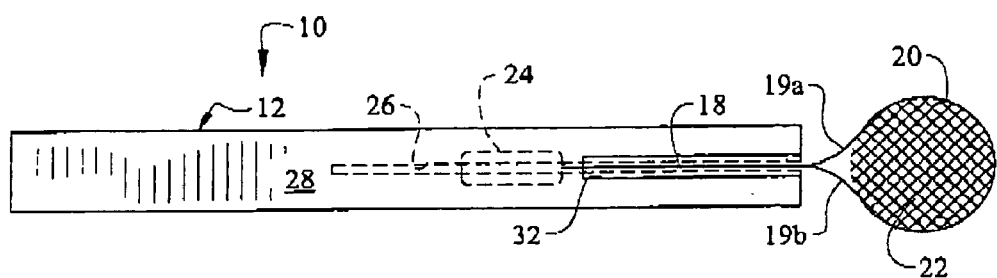
FIG. 4 is a bottom plan view of the illustrative embodiment in said fully extended configuration.
Figure 5:
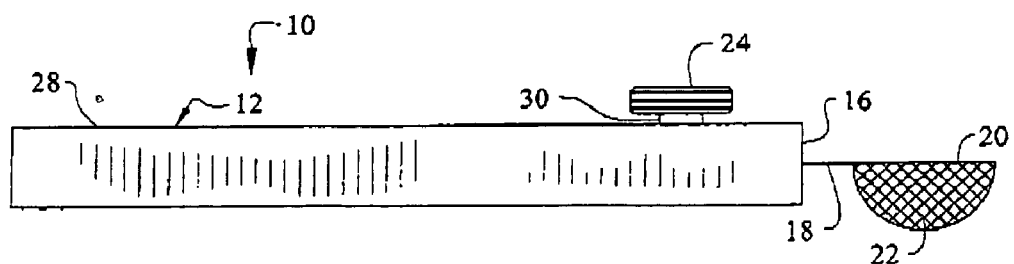
FIG. 5 is a side elevational view of the illustrative embodiment in its fully extended configuration.

FIG. 4 provides a bottom view of novel tool 10 when said tool is in its FIG. 3 configuration and FIG. 5 provides a side elevational view thereof when said tool is in said FIG. 3 configuration.

Control member 24 controls the instantaneous position of handle 18 and hence of rim 20 and net 22. Control member 24 is slideably mounted for movement along the extent of slot 18 as indicated by double-headed directional arrow 25 in FIGS. 1-3. A thumb of a user easily engages control member 24 when tool 10 is held in a user's palm, supported by the fingers of the user.

Figure 7:
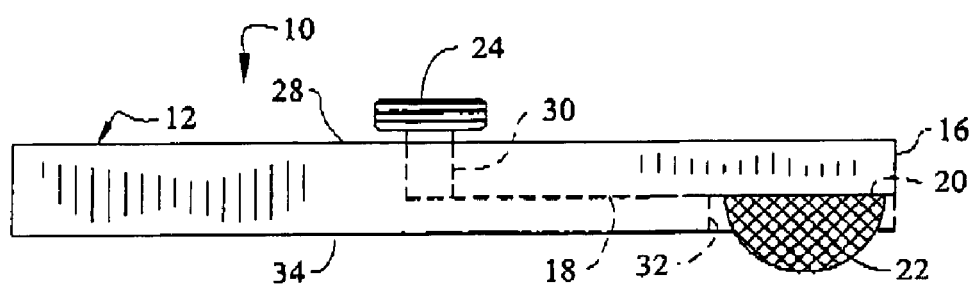
FIG. 7 is a side elevational view of the illustrative embodiment in said fully retracted configuration.

Elongate 26 is formed in top wall 28 of base 12 and has a length substantially equal to the length of elongate bore 14. However, the width of slot 26 is less than that of elongate bore 14 to prevent escape of handle 18, rim 20, and net 22 therefrom. Rigid rod 30, part of which is depicted in FIGS. 5 and 7, has a width slightly less than the width of slot 26 and interconnects control member 24 and handle 18. Accordingly, sliding movement of control member 24 along the extent of base 12 effects simultaneous and corresponding movement of handle 18, rim 20 and net 22.

Net 22 has an upper peripheral edge mounted about the periphery of rim 20 as aforesaid. Said net further includes a main body, integral with said upper edge, that depends from said upper edge and which performs the foreign body capturing function of this invention.

Figure 6:
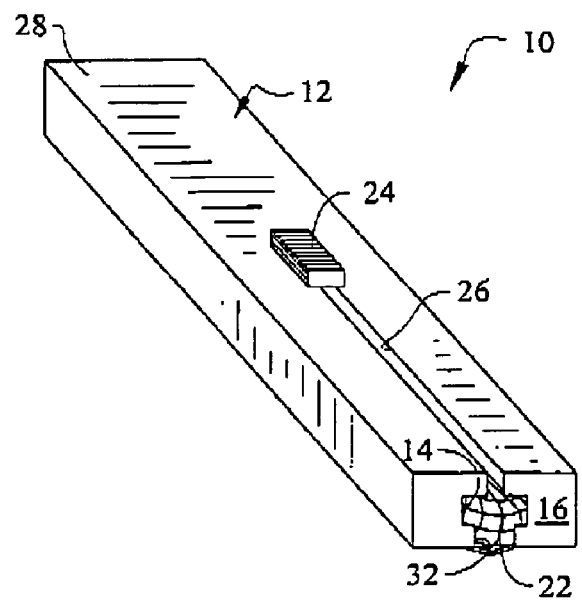
FIG. 6 is an isometric view of the illustrative embodiment in its fully retracted configuration.

As best understood in connection with FIGS. 4-7, net 22 is not fully housed within elongate bore 14 when handle 18 is in its fully retracted position. More particularly, FIGS. 4, 6, and 7 depict slot 32 which is truncate in extent relative to the extent of elongate slot 26. Truncate slot 32 is formed in bottom wall 34 of elongate base 12, is parallel to elongate bore 14, and is in open communication with the leading half, approximately, of said elongate bore 18. Thus, as indicated in FIGS. 6 and 7, the main body of net 22 depends from rim 20 even when rim 20 is fully retracted within elongate bore 18 and the lower end of the main body of the net extends below said bottom wall 34.

In this illustrative embodiment, the width of truncate slot 32 is greater than the width of elongate slot 26 but less than the width of elongate bore 14. This difference in widths creates a shoulder that retains rim 20 within elongate bore 14 when handle 18 is in its fully retracted configuration.

Net 22 is formed of a flexible material such an elastic fabric that remains firmly attached to rim 20 as said rim changes from a substantially linear shape to that of a circle or ellipse and from said circular or elliptical shape back to said substantially linear shape as handle 18 is extended and retracted, respectively.

As best understood by comparing FIGS. 1-3, handle 18 is bifurcated at its leading end and the branches formed by the bifurcation form the trailing end of rim 20. Thus there is a smooth, arcuate transition from handle 18 to rim 20. Said arcuate transition is denoted 19a, 19b in FIGS. 3 and 4 but it should be understood that said handle and rim are formed integrally with one another as aforesaid. This ensures that rim 20 and hence net 22 are not fully open until the respective trailing ends of said arcuate transition regions 19a, 19b have fully cleared said elongate bore 14. Arcuate transition regions 19a, 19b also enable facile retraction of rim 20 and net 22 by causing a gradual compression of said rim as its re-enters elongate bore 14. Accordingly, rim 20 is restored to its narrow profile as its exits the incision.

More particularly, handle 18 is bifurcated at a leading end thereof to form a pair of branches. The pair of branches includes a first branch having a first arcuate curve formed therein and a second branch having a first arcuate curve formed therein. The first branch first arcuate curve and the second branch first arcuate curve diverge from one another in a common plane when in repose. The first branch has a second arcuate curve formed therein and the second branch has a second arcuate curve formed therein. The respective second arcuate curves of the first and second branches converge toward one another when in repose so that the first and second branches cooperate to form the rim of the foreign body capturing means. The rim has a substantially linear configuration when it is fully received within the elongate bore and has an elliptical configuration when fully extended from the elongate bore. The first arcuate curve of the first branch and the first arcuate curve of the second branch cooperate with one another to facilitate entry of the rim into the elongate bore when the foreign body capturing means is moved from its fully extended configuration to its fully retracted configuration.

Tool 10 enables a surgeon to remove even very large intraocular foreign bodies through a small incision. Elongate base 12 is not introduced into the incision. Leading end 16 of base 12 is placed in alignment with an incision with handle 18 in its fully retracted position. The physician then advances control member 24 in a trailing-to-leading direction, thereby causing the extension of handle 18 and the introduction of rim 20 and net 22 through the incision. Rim 20 does not begin to expand under its inherent bias until the trailing end of said rim has fully cleared leading end 16 of elongate bore 14. This enables the rim to enter the incision while still in its narrow profile configuration.

Thus, when rim 20 and net 22 are fully inserted through the incision, said parts are fully open and the physician can capture very large intraocular bodies in said net. The foreign body or bodies remain in the net when the net is returned to its fully retracted configuration by sliding control member 24 in a leading-to-trailing direction. The rim is restored to its narrow profile as it exits the incision due to the gradual curvature of the trailing end of the rim.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A surgical tool for capturing and removing intraocular foreign bodies, comprising:
   an elongate base;
   an elongate bore formed in said elongate base, said elongate bore having a leading end in open communication with a leading end of said elongate base;
   a foreign body capturing means slideably received within said elongate bore;
   said foreign body capturing means including an elongate handle, a rim, and a net;
   a control member connected to said foreign body capturing means for controlling the instantaneous position of said foreign body capturing means;
   said foreign body capturing means having a fully retracted position where said foreign body capturing means is substantially received within said elongate bore, a fully extended position where said foreign body capturing means is fully extended from said elongate bore, and an infinite number of functional positions of adjustment therebetween;
   an elongate slot formed in a top wall of said elongate base in parallel relation to said elongate bore;
   said elongate slot having a length substantially equal to a length of said elongate bore;
   said control member being slideably mounted to said top wall of said elongate base;
   said control member having a fully retracted position, a fully extended position, and an infinite number of functional positions of adjustment therebetween;
   a rigid rod extending through said elongate slot and interconnecting said control member and said handle of said foreign body capturing means;
   said fully retracted position of said control member corresponding to said fully retracted position of said foreign body capturing means and said fully extended position of said control member corresponding to said fully extended position of said foreign body capturing means;
   said elongate slot having a width less than a width of said elongate bore;
   a truncate slot formed in a bottom wall of said elongate base in parallel relation to said elongate bore;
   said truncate slot having a length less than said length of said elongate bore;
   said truncate slot having a leading end in open communication with said leading end of said elongate base;
   said truncate slot having a length equal to about half that of said elongate bore and being in open communication with a leading half of said elongate bore;
   said net having an upper end mounted about a perimeter of said rim and said net having a main body, integral with said upper end, that depends from said upper end when said foreign body capturing means is in fully retracted position, said fully extended position, and said infinite member of functional positions of adjustment therebetween;
   said truncate slot having a width greater than a width of said elongate slot but less than a width of said elongate bore, said width difference creating a shoulder that supports said rim when said foreign body capturing means is in said fully retracted position; and
   said net extending below said bottom wall of said elongate base when said foreign body capturing means is in said fully retracted position, and said net extending below a plane defined by said bottom wall of said elongate base when said foreign body capturing means is in said fully extended position and any of said infinite number of functional positions of adjustment between said fully extended and fully retracted positions.

2. The tool of claim 1, further comprising:
   said handle being bifurcated at a leading end thereof to form a pair of branches;
   said pair of branches including a first branch having a first arcuate curve formed therein and a second branch having a first arcuate curve formed therein;
   said first branch first arcuate curve and said second branch first arcuate curve diverging from one another in a common plane when in repose;
   said first branch having a second arcuate curve formed therein and said second branch having a second arcuate curve formed therein;
   said respective second arcuate curves of said first and second branches converging toward one another when in repose so that said first and second branches cooperate to form said rim of said foreign body capturing means;
   said rim having a substantially linear configuration when said rim is fully received within said elongate bore;
   said rim having an elliptical configuration when fully extended from said elongate bore;
   said first arcuate curve of said first branch and said first arcuate curve of said second branch cooperating to facilitate entry of said rim into said elongate bore when said foreign body capturing means is moved from its fully extended configuration to its fully retracted configuration.

3. The tool of claim 1, further comprising:
   said rim being formed of a metallic material.

4. The tool of claim 1, further comprising:
   said rim being formed of a polymeric material.

5. The tool of claim 1, further comprising:
   said net being formed of a fabric mesh.

* * * * *